US011583191B2

(12) United States Patent
Schmitt et al.

(10) Patent No.: US 11,583,191 B2
(45) Date of Patent: Feb. 21, 2023

(54) APPARATUS AND METHOD FOR DETERMINING BLOOD PRESSURE OF A SUBJECT

(71) Applicant: KONINKLIJKE PHILIPS N.V., Eindhoven (NL)

(72) Inventors: Lars Schmitt, Aachen (DE); Jens Muehlsteff, Aachen (DE); Erik Bresch, Eindhoven (NL); Xinchi Yu, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 247 days.

(21) Appl. No.: 16/630,900

(22) PCT Filed: Jul. 23, 2018

(86) PCT No.: PCT/EP2018/069894
§ 371 (c)(1),
(2) Date: Jan. 14, 2020

(87) PCT Pub. No.: WO2019/016405
PCT Pub. Date: Jan. 24, 2019

(65) Prior Publication Data
US 2020/0229716 A1    Jul. 23, 2020

(30) Foreign Application Priority Data

Jul. 21, 2017  (EP) ..................................... 17182479

(51) Int. Cl.
*A61B 5/021* (2006.01)
*A61B 5/00* (2006.01)
(Continued)

(52) U.S. Cl.
CPC ........ *A61B 5/02108* (2013.01); *A61B 5/0095* (2013.01); *A61B 5/7246* (2013.01);
(Continued)

(58) Field of Classification Search
None
See application file for complete search history.

(56) References Cited

U.S. PATENT DOCUMENTS

| 5,533,511 A | * | 7/1996 | Kaspari ............. A61B 5/02007 600/494 |
| 6,196,974 B1 | | 3/2001 | Miwa |

(Continued)

FOREIGN PATENT DOCUMENTS

JP    2000033078 A    2/2000

OTHER PUBLICATIONS

Yue Wu: "Triggering of NIBP Measurements Based on PPG Features"; Thesis Paper, Eindhoven University of Technology, 2014, 13 Page Document.

(Continued)

*Primary Examiner* — Yi-Shan Yang (57) ABSTRACT

The present invention relates to an apparatus and method for determining blood pressure of a subject. To automatically trigger calibration the apparatus comprises a sensor signal input configured to obtain an arterial pulse wave sensor signal of the subject, a feature extraction unit configured to extract multiple features from the obtained arterial pulse wave sensor signal, an estimation unit configured to determine multiple blood pressure estimation values for individual extracted features and/or groups of extracted features and to determine the subject's blood pressure from said multiple blood pressure estimation values, a calibration unit configured to calibrate the estimation unit based on blood pressure reference measurements, and a calibration trigger unit configured to trigger calibration by the calibration unit if the multiple blood pressure estimation values diverge more than a divergence limit.

10 Claims, 6 Drawing Sheets

(51) Int. Cl.
*A61B 8/04* (2006.01)
*A61B 8/08* (2006.01)
*A61B 8/00* (2006.01)

(52) U.S. Cl.
CPC .............. *A61B 5/7275* (2013.01); *A61B 8/04* (2013.01); *A61B 8/5223* (2013.01); *A61B 8/58* (2013.01); *A61B 2560/0223* (2013.01); *A61B 2562/0219* (2013.01)

(56) References Cited

U.S. PATENT DOCUMENTS

| | | | |
|---|---|---|---|
| 7,455,643 | B1 | 11/2008 | Li et al. |
| 9,289,136 | B2 | 3/2016 | Addison et al. |
| 10,194,811 | B2 | 2/2019 | Ohno |
| 2008/0228089 | A1* | 9/2008 | Cho .................. A61B 5/02125 600/485 |
| 2010/0081945 | A1 | 4/2010 | Sethi |
| 2011/0077531 | A1* | 3/2011 | Watson ................ A61B 5/0205 702/19 |
| 2011/0245690 | A1* | 10/2011 | Watson .................. A61B 5/022 600/509 |
| 2012/0136261 | A1 | 5/2012 | Sethi et al. |
| 2016/0166160 | A1 | 6/2016 | Casale |
| 2017/0042433 | A1 | 2/2017 | Noh et al. |

OTHER PUBLICATIONS

Couceiro et al: "Real-Time Prediction of Neurally Mediated Syncope"; IEEE Journal of Biomedical and Health Informatics, 2015, pp. 1-13.
Monte-Moreno: "Non-Invasive Estimate of Blood Glucose and Blood Pressure From a Photoplethysmograph by Means of Machine Learning Techniques"; Artifical Intelligence in Medicine 53 (2011), pp. 127-138.
Mukkamala et al: "Toward Ubiquitous Blood Pressure Monitoring via Pulse Transit Time Theory and Practice"; IEEE Transactions on Biomedical Engineering, vol. 62, No. 8, Aug. 2015, pp. 1879-1901.
PCT/EP2018/069894, ISR & WO, dated Oct. 26, 2018, 16 Page Document.

* cited by examiner

APPARATUS AND METHOD FOR DETERMINING BLOOD PRESSURE OF A SUBJECT

CROSS-REFERENCE TO PRIOR APPLICATIONS

This application is the U.S. National Phase application under 35 U.S.C. § 371 of International Application No. PCT/EP2018/069894, filed on Jul. 23, 2018, which claims the benefit of European Patent Application No. 17182479.0, filed on Jul. 21, 2017. These applications are hereby incorporated by reference herein.

FIELD OF THE INVENTION

The present invention relates to an apparatus and a method for determining blood pressure of a subject. Further, the present invention relates to an apparatus for monitoring blood pressure of a subject.

BACKGROUND OF THE INVENTION

Blood pressure (BP) measurements are common in all hospital settings to assess and monitor the hemodynamic status of a patient. For instable patients continuous monitoring is required for which currently mostly an invasive intra-arterial pressure catheter is used. This method requires trained medical staff to apply and is associated with an infection risk for a patient. However, if the hemodynamic stability of the patient allows for, non-invasive measurement methods (auscultatory or oscillometric) are applied. These methods involve a cuff, which is typically applied at the upper arm. This method does not allow to continuously monitor blood pressure and is rather uncomfortable for the patient, in particular when automated spot-check measurements with e.g. 15 minutes intervals are conducted during night.

Further methods allow for continuous, yet unobtrusive measurement of blood pressure, preferably without applying any external force or pressure to the patient. These methods are typically based on physiological parameters that can be sensed continuously and non-invasively. From the periodic waveform data a BP surrogate parameter is calculated, which allows to derive BP information on a continuous or beat-to-beat basis. An example for a BP surrogate parameter is pulse-arrival-time (PAT), which can be computed on a beat-by-beat basis from continuous electrocardiogram (ECG) and photoplethysmogram (PPG) waveform data. PAT represents the time of arrival of the arterial pulse at the location of measurement. With increasing/decreasing BP, the pulse waves travel faster/slower through the arterial tree, therefore resulting in decreased/increased PAT. In principle, the photoplethysmographic, electrocardiographic, and seismocardiographic waveform signals obtained from electrical, optical, and accelerometry sensors contain rich physiological information, from which different features can be extracted for determining a surrogate for BP.

US 2012/0136261 A1 discloses systems and methods for calibrating the calculation of physiological parameters. Two or more calibration techniques may be used to determine a relationship between physiological measurements and a desired physiological parameter, such as a relationship between differential pulse transit time (DPTT) and blood pressure. Different calibration techniques may be used in a serial fashion, one after the other, or in a parallel fashion, with different weights accorded to each calibration technique. When physiological or other changes occur, the calibration data may be stored for later use and new calibration data may be generated.

US 2017/0042433 A1 discloses a blood pressure estimating method including measuring a biosignal including pulse wave information of a user, determining a calibration method for a blood pressure estimation model, calibrating the blood pressure estimation model using the determined calibration method, and estimating a blood pressure of the user from the biosignal using the calibrated blood pressure estimation model.

There is still a need for feature selection that is robust to inter-patient as well as intra-patient variability and/or for automatically detecting when (re-)calibration is required.

SUMMARY OF THE INVENTION

It is an object of the present invention to provide an apparatus and method for determining blood pressure of a subject, which automatically detect when (re-)calibration is required.

In a first aspect of the present invention an apparatus for determining blood pressure of a subject is presented comprising:
  a sensor signal input configured to obtain an arterial pulse wave sensor signal of the subject,
  a feature extraction unit configured to extract multiple features from the obtained arterial pulse wave sensor signal,
  an estimation unit configured to determine multiple blood pressure estimation values for individual extracted features and/or groups of extracted features and to determine the subject's blood pressure from said multiple blood pressure estimation values,
  a calibration unit configured to calibrate the estimation unit based on blood pressure reference measurements, and
  a calibration trigger unit configured to trigger calibration by the calibration unit if the multiple blood pressure estimation values diverge more than a divergence limit.

In a further aspect of the present invention an apparatus for monitoring blood pressure of a subject is presented comprising:
  an arterial pulse wave sensor configured to acquire an arterial pulse wave sensor signal of the subject,
  a blood pressure reference measurement unit configured to acquire blood pressure reference measurements of the subject, and
  an apparatus as disclosed herein for determining blood pressure of a subject based on the acquired arterial pulse wave sensor signal and the acquired blood pressure reference measurements.

In yet further aspects of the present invention, there are provided a corresponding method, a computer program which comprises program code means for causing a computer to perform the steps of the method disclosed herein when said computer program is carried out on a computer as well as a non-transitory computer-readable recording medium that stores therein a computer program product, which, when executed by a processor, causes the method disclosed herein to be performed.

Preferred embodiments of the invention are defined in the dependent claims. It shall be understood that the claimed method, apparatus, computer program and medium have similar and/or identical preferred embodiments, in particular as defined in the dependent claims and as disclosed herein.

The present invention is based on the idea to make use of a trigger for triggering (re-)calibration (generally called "calibration" herein) if selected features used for determining the blood pressure lose their relation to blood pressure. This situation is automatically detected. The problem of determining the need for calibration for a set of features is thus addressed by using multiple blood pressure estimation values for individual extracted features and/or groups of extracted features, from which the subject's blood pressure is determined, and to trigger calibration if the multiple blood pressure estimation values diverge more than a divergence limit.

Hence, the present invention does not determine if a blood pressure change determined by comparing a most recent blood pressure measurement to one or more preceding blood pressure measurements (i.e. blood pressure measurements obtained at different moments in time) exceeds a particular threshold (as done according to US 2012/0136261 A1). Further, the present invention does not determine if the degree of similarity between a reference biosignal (e.g. a PPG signal) selected from a plurality biosignals measured by a plurality of sensors at different locations and a biosignal prestored in a template is less than or equal to a predetermined threshold (as done according to US 2017/0042433 A1). Instead, the present invention determines two or more blood pressure estimation values, wherein each blood pressure estimation value is determined for a different feature or a different group of features extracted from the (same) obtained arterial pulse wave sensor signal, e.g. a PPG signal.

For instance, as proposed in an embodiment, a feature divergence metric is introduced, which measures the difference between the BP estimates across the set of selected features, thereby providing a more direct and reliable way of detecting when calibration is needed. The calibration trigger unit may hence be configured to determine a feature divergence metric, the feature divergence metric representing a metric for the difference between the multiple blood pressure estimation values. The divergence metric may then be compared to a divergence threshold (or limit) to detect if calibration is needed or not.

In a practical embodiment the calibration trigger unit is configured to trigger calibration if the average difference, maximum difference or standard deviation of the differences of a predetermined number or all of said multiple blood pressure estimation values exceeds a divergence threshold.

Hereby, the calibration trigger unit is preferably configured to use a predetermined or time-varying divergence threshold, in particular wherein the time-varying divergence threshold is reduced with time since the last calibration. This ensures that at some point in time a calibration will be made and is the need for calibration is not completely suppressed.

In an implementation the calibration unit is configured to determine calibration values for determining said multiple blood pressure estimation values for individual extracted features and/or groups of extracted features by said estimation unit by fitting a modelled relation between an extracted feature or group of extracted features and blood pressure to the actually extracted feature value or group of extracted feature values and the blood pressure reference measurements, in particular via linear or non-linear regression.

In a simple embodiment the estimation unit is configured to determine the subject's blood pressure by taking the average or median of some or all of said multiple blood pressure estimation values.

Preferably, the estimation unit is configured to determine the subject's blood pressure by taking a weighted average of some or all of said multiple blood pressure estimation values, wherein said weights used for said weighted average are determined based on a correlation between a subject's blood pressure and its corresponding feature, in particular wherein said correlation between a subject's blood pressure and its corresponding feature is determined based on the obtained blood pressure reference measurements. As the true blood pressure is not known, the blood pressure reference measurements may be used to assess the correlation. Features that show good correlation with blood pressure may be selected and for each selected feature a blood pressure estimation value can be calculated (e.g. via regression according to a mathematical model, using again the blood pressure reference measurements). If there are multiple features selected, the multiple blood pressure estimation values may be combined into a single blood pressure estimation value, which can be done via weighted averaging or other means.

In an alternative embodiment said estimation unit is configured to determine the subject's blood pressure by taking a weighted average of some or all of said multiple blood pressure estimation values, wherein said weights used for said weighted average are determined by selecting a blood pressure estimation value with its corresponding feature having the best correlation with the subject's blood pressure, or depending on a signal-to-noise ratio of a corresponding feature of the blood pressure estimation value, or based on a regression error.

Another problem with existing systems and methods is the lack of a method for feature selection that is robust to inter-patient as well as intra-patient variability. This problem is addressed by the embodiment according to which the calibration unit is configured to perform an initial calibration of the estimation unit for all extracted features and to select a subset of extracted features based on a correlation between a subject's blood pressure and a corresponding feature and the estimation unit is configured to determine the multiple blood pressure estimation values for individual extracted features and/or groups of extracted features of said subset. In this way an automatic feature selection is provided, where for an individual patient a subset of features out of a large pool of possible features is automatically and individually selected. Preferably, the set of selected features is dynamically updated during every calibration.

Hereby, the calibration unit may be configured to repeat the initial calibration of the estimation unit for some or all extracted features if one or more correlation values of said correlation for one or more features and the subject's blood pressure are below a correlation threshold. Alternatively, the calibration unit may be configured to repeat the calibration of the estimation unit for some or all extracted features if one or more correlation values of said correlation for one or more features and the subject's blood pressure are below a correlation threshold.

The present invention also provides an apparatus for monitoring blood pressure of a subject comprising an arterial pulse wave sensor, a blood pressure reference measurement unit an apparatus as disclosed herein for determining blood pressure of a subject. The arterial pulse wave sensor may include one or more of an accelerometer, a photoplethysmography sensor, an ultrasonic sensor, a radar sensor, and a vital sign camera.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE EMBODIMENTS

Figure 1:
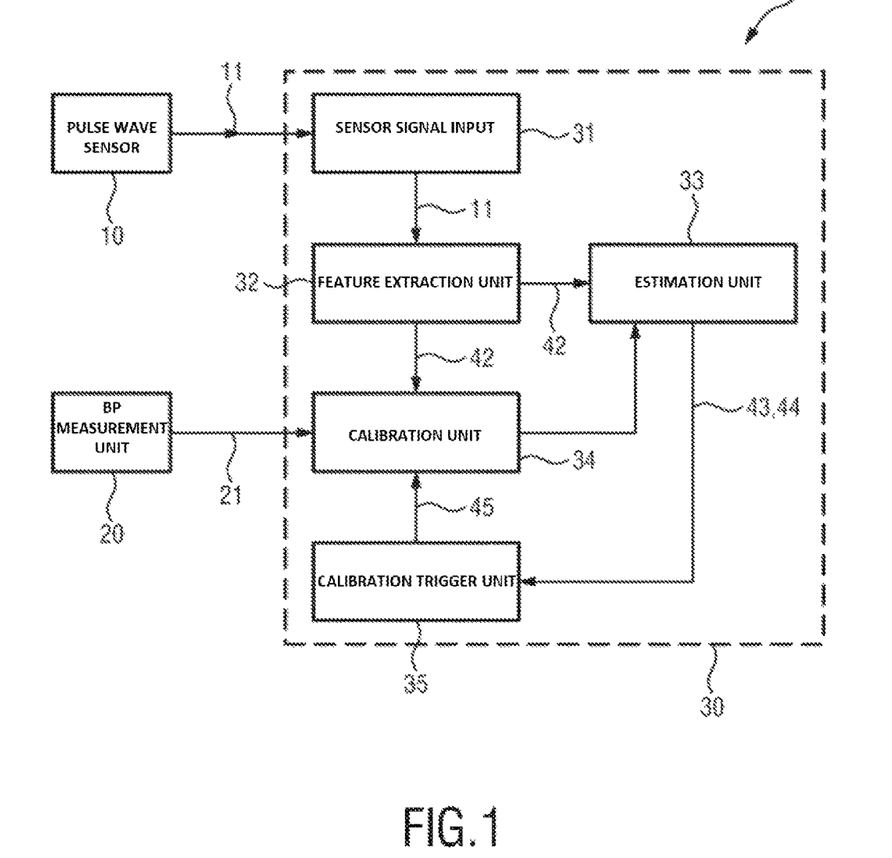
FIG. 1 shows an embodiment of an apparatus for monitoring blood pressure and an apparatus for determining blood pressure according to the present invention.

FIG. 1 shows an embodiment of an apparatus 1 for monitoring blood pressure and an apparatus 30 for determining blood pressure of a subject, e.g. a patient, according to the present invention. The apparatus 1 for monitoring blood pressure comprises an arterial pulse wave sensor 10 configured to acquire an arterial pulse wave sensor signal 11 (or multiple arterial pulse wave sensor signals) of the subject. The arterial pulse wave sensor 10 comprises one or more of an accelerometer, a photoplethysmography (PPG) sensor, an ultrasonic sensor, a radar sensor, and a vital sign camera. The apparatus 1 further comprises a blood pressure reference measurement unit 20 configured to acquire blood pressure reference measurements 21 of the subject. The blood pressure reference measurement unit 20 may e.g. be a conventional non-invasive BP (e.g. a NIBP) measurement device. The apparatus 1 further comprises the apparatus 30 for determining blood pressure of a subject based on the acquired arterial pulse wave sensor signal 11 and the acquired blood pressure reference measurements 21. The apparatus 30 may be implemented in soft- and/or hardware, e.g. as an appropriately programmed processor, CPU or computer.

A means, such as a belt, sticker, etc., for attachment or positioning of the sensor 10 and/or the unit 20 may be provided if needed.

The apparatus 30 for determining blood pressure of a subject comprises a sensor signal input 31 configured to obtain the arterial pulse wave sensor signal 11 of the subject. The sensor signal input 31 may e.g. be a wireless or wired interface (e.g. an USB interface, a WLAN interface, a network interface, etc.) for retrieving or receiving the arterial pulse wave sensor signal 11 either directly from the arterial pulse wave sensor 10 or from a storage or buffer.

The apparatus 30 further comprises a feature extraction unit 32 configured to extract multiple features 42 from the obtained arterial pulse wave sensor signal 11. There are generally a large number of features, which may be used, e.g. time between characteristic points, amplitudes of characteristic points, etc. of the obtained arterial pulse wave sensor signal 11.

The apparatus 30 further comprises an estimation unit 33 configured to determine multiple blood pressure estimation values 43 for individual extracted features 42 and/or groups of extracted features 42 and to determine the subject's blood pressure 44 from said multiple blood pressure estimation values 43. A calibration unit 34 calibrates the estimation unit 33 based on the extracted features 42 and the blood pressure reference measurements 21, which may be stored in the apparatus 30 or obtained (retrieved or received), e.g. directly or via the input unit 31, from the blood pressure reference measurement unit 20 or from the storage or buffer. A calibration trigger unit 35 triggers calibration by the calibration unit 34 (e.g. through a trigger signal 45) if the multiple blood pressure estimation values 43 diverge more than a divergence limit, which may be a predetermined or time-varying threshold and which may be stored in the apparatus 30 or obtained from an external entity.

Figure 2:
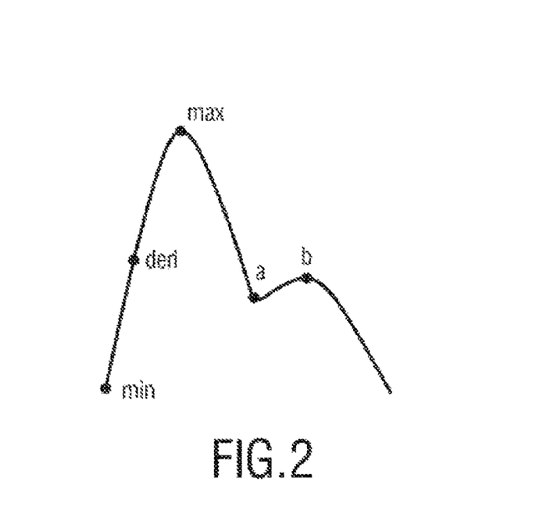
FIG. 2 shows a diagram of a PPG waveform signal indicating characteristic points.

FIG. 2 shows a diagram of a PPG waveform signal, representing an example arterial pulse wave sensor signal 11, indicating characteristic points (features). In this example these points include minimum of the PPG pulse (min), maximum of PPG pulse (max), maximum of first derivative (deri), minimum and maximum of the dicrotic notch (a and b). Examples of features that can be extracted from the PPG waveform signal as these can be found in literature are shown in the following table:

| NO. | Feature | Definition |
|---|---|---|
| 1 | amp_deri/max | amplitude of maximum of first derivative/amplitude of maximum of PPG |
| 2 | time_deri2a | time from maximum of first derivative to minimum of dicrotic notch* in PPG |
| 3 | time_deri2b | time from maximum of first derivative to maximum of dicrotic notch* in PPG |
| 4 | time_max2a | time from PPG maximum to minimum of dicrotic notch* in PPG |
| 5 | time_max2b | time from PPG maximum to maximum of dicrotic notch* in PPG |
| 6 | time_pulse | pulse time |
| 7 | time_sys | systolic time: time from PPG minimum to PPG maximum |
| 8 | time_dias | diastolic time: time from PPG maximum to the end of the pulse |
| 9 | time_dias_sys | diastolic time/systolic time |
| 10 | area_a | area from PPG minimum to the minimum of the dicrotic notch*/area from the minimum of the dicrotic notch* to the end of the pulse |
| 11 | area_b | area from PPG minimum to the maximum of the dicrotic notch*/area from the maximum of the dicrotic notch* to the end of the pulse |
| 12 | width_⅔ | pulse width at ⅔ of the pulse amplitude |
| 13 | width_½ | pulse width at ½ of the pulse amplitude |
| 14 | area_sys_dias | area of systolic component/area of diastolic component of the pulse |
| 15 | curve_sys_dias | curve length from PPG minimum to PPG maximum/curve length from PPG maximum to the end of the pulse |

(a) Time Domain Features

| Feature | Definition |
|---|---|
| f_NHA | $\sum_{i=2}^{n} FFT(fi)^2 / \sum_{i=1}^{n} FFT(fi)^2$ |
| f_NHA2 | $\sum_{i=2}^{n} FFT(fi) / \sum_{i=1}^{n} FFT(fi)$ |

| Feature | Definition |
| --- | --- |
| f_NHA3 | FFT(f2)/FFT(f1) |
| f_diff | f2 − f1 |
| f_area1 | area under curve for frequency larger than f2/area under curve for frequency larger than f1 |
| f_area2 | area under curve for frequency larger than f2/total area under curve |

(b) Frequency Domain Features

| Feature | Definition |
| --- | --- |
| w__1/E5 | reciprocal of the percentage of energy of D5 |
| w__E6/E5 | the percentage of energy of D6/the percentage of energy of D5 |
| w__E5/E4 | the percentage of energy D5/the percentage of energy of D4 |
| w__a1__456 | amplitude ratio of reflected wave peak and direct wave peak on P__456 |
| w__a2__456 | squared amplitude ratio of reflected wave peak and direct wave peak on P__456 |
| w__t__456 | time__max2b on P__456 |
| w__a1__45 | amplitude ratio of reflected wave peak and direct wave peak on P__45 |
| w__a2__45 | squared amplitude ratio of reflected wave peak and direct wave peak on P__45 |
| w__t__45 | time__max2b on P__45 |

(c) Wavelet Domain Features

Due to inter-patient variability, particular BP surrogate parameters have stronger correlation with BP in some patients and less correlation with BP in other patients. Also, surrogate parameters need to be calibrated to blood pressure for an individual patient in order to allow for quantitative estimation. To give an example: the height of a patient determines the length of the arterial tree and is therefore one factor among many that contributes to inter-patient variability when using PAT as a surrogate parameter.

A standard method for calibration is as follows: A mathematical model for relating the surrogate parameter to BP is defined, containing one or more unknown calibration parameters. Multiple pairs of surrogate parameter values and reference BP values (typically with a cuff device) are measured. The calibration constants are determined by fitting the model to the BP-surrogate parameter pairs (regression). Afterwards blood pressure can be estimated from the continuously measured surrogate parameter via the defined mathematical model by utilizing the determined calibration constants.

The calibration process needs to be regularly repeated (recalibration) to account for intra-patient variability. As an example vascular compliance can change due to certain physiological event or due to medication such that the calibration parameters need to be updated. Furthermore, changes in the vascular state of a patient can even affect the correlation of a particular surrogate parameter with BP, such that recalibration only partly accounts for intra-patient interoperability.

Thus, there are two major challenges for using BP surrogates, namely identifying good surrogate parameters that correlate well with BP, always and for all patients, and detecting when calibrated surrogate parameters need recalibration. The challenge with the latter challenge is that recalibration is needed when the BP estimation performance degrades. However, a direct assessment of the BP estimation performance is not possible, as reference BP measurements are not available.

In an embodiment a calibration method used according to the present invention comprises obtaining and storing one or more reference blood pressure measurements from the NIBP device, assessing the relation between each feature and blood pressure (e.g. correlation coefficient with p-value), based on the stored reference blood pressure measurements, selecting a subset of the strongest features (those with best relation to blood pressure), and determining the calibration parameters for each feature, based on the stored blood pressure reference measurements (e.g. via linear or non-linear regression).

According to an embodiment of the blood pressure estimation method according to the present invention for each selected feature blood pressure is estimated via a functional relation (e.g. linear model) by using the calibration parameters, and the blood pressure estimates of each selected feature are combined into a single blood pressure estimate (surrogate), e.g. by taking the median or by means of averaging.

According to an embodiment of a method for automatically triggering recalibration (i.e. determining if and when to recalibrate), recalibration is triggered if the selected features lose their relation to blood pressure. This situation may be automatically detected by comparing a feature divergence metric (FDM) with a threshold (which is optionally time-varying). An FDM represents a metric for the difference between the BP estimates from the selected individual features (e.g. the maximum difference or the standard deviation).

An embodiment of the method for recalibration uses the steps of the calibration method described above: The set of selected features and their calibration parameters is dynamically updated. The influence of older stored reference blood pressure measurements for recalibration may be reduced (e.g. either by removing them from the storage or by assigning proper weighting factors).

Figure 3:
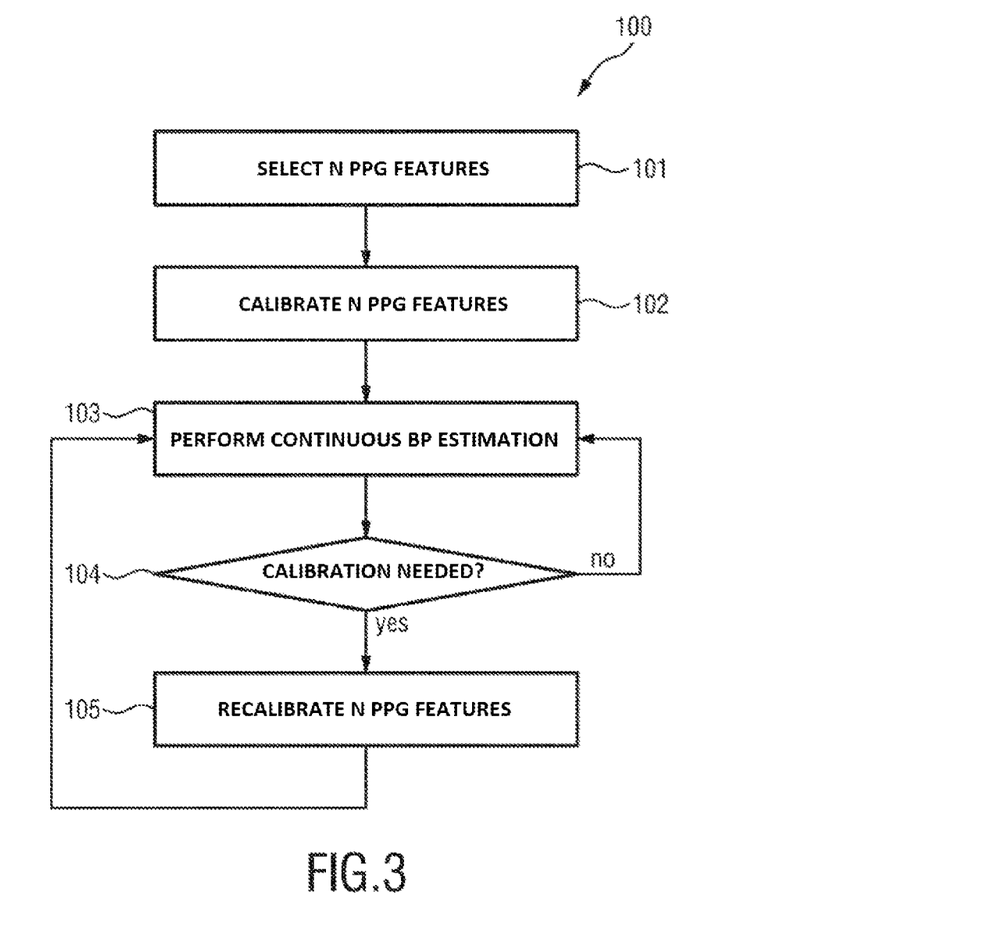
FIG. 3 shows a flow chart of a first embodiment of a method according to the present invention.

FIG. 3 shows a flow chart of a first embodiment of a method 100 according to the present invention. This embodiment deals with automatic recalibration of multiple features that are used for continuous BP estimation.

In a first step 101 N PPG signal features are selected. The selection of features is based on functions that can be applied to the PPG waveform signal and provide a feature value. As an example, the feature time_deri2a (time from maximum of first derivate to minimum of dicrotic notch) from the table shown above may be used. For every pulse beat, the feature value is obtained by extracting the time difference in the PPG waveform signal that corresponds to the maximum of the first derivative to the minimum of the dicrotic notch.

As an alternative option, a different physiological signal, other than a PPG signal (e.g. an ECG signal) could be used. Also, a combination of multiple physiological signals can be used. For example, the feature PAT is extracted from two different physiological signals, the electrocardiogram and the photoplethysmogram. Furthermore, for each feature a mathematical model is defined to relate the feature to BP in terms of several unknown calibration parameters. These can be linear or non-linear models. For example, a linear model involves two calibration parameters, one for the slope and one for the offset. A meaningful preselection of N features could be based on common knowledge of features that are known to correlate well with BP in general. Alternatively, the preselection of features could be based on a dedicated data collection study on subjects. In this particular embodiment for continuous BP estimation the set of preselected features is not adapted to an individual patient, but rather is the same for all patients and remains fixed during the complete monitoring procedure.

In a second step 102 an initial calibration of the N features is conducted. For this purpose a number of BP reference measurements are obtained with a blood pressure measurement device (typically a non-invasive device). This device could e.g. be a cuff device or another calibrated NIBP device. The BP reference measurement values and the corresponding feature values at time of the reference measurements are stored. Subsequently, for each feature the calibration parameters are determined by fitting the modelled relation between the feature and BP to the actual measured pairs of feature values and BP reference measurement values. Typically this is done via regression, linear or non-linear depending on the modelled relation.

In a third step 103, continuous BP estimation is performed. For each feature, the feature value is extracted from the received physiological signals. Subsequently, from each feature value the corresponding BP value is estimated by using the modelled mathematical relation with BP and the determined calibration parameters. Finally, the BP values estimated from all features are combined into a single estimated BP value. The combination can be done by various methods. In a preferred embodiment, the median of the estimated BP values from all features is chosen. To give some examples of alternative options, the combination could be done by averaging or by weighted averaging. The weighting factors could be chosen according to the correlation between the respective features and BP, where the correlation is determined from the measurements during the calibration procedure. Another alternative would be to select that estimated BP value, which corresponds to the feature that has the best correlation.

Figure 4:
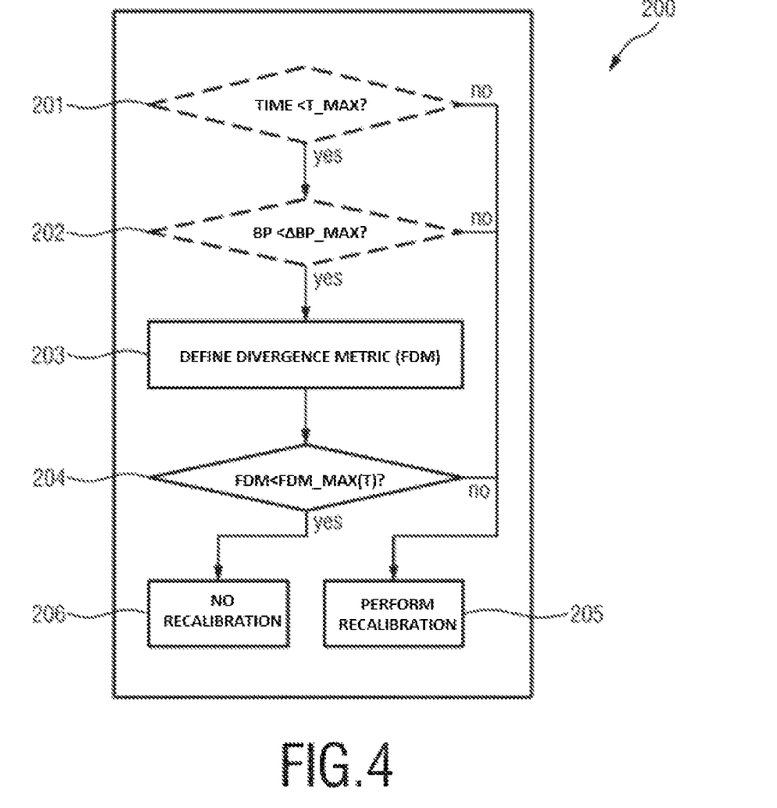
FIG. 4 shows a flow chart of a second embodiment of a method according to the present invention.

In a fourth step 104, the need for recalibration is detected ("recalibration condition satisfied?"). This step could be conducted immediately, after or during the previous step 103 in which a single new estimated BP value has been determined, or alternatively, after a couple of new estimated BP values have been determined. An embodiment of an automatic procedure 200 for determining the need for recalibration (i.e. an embodiment of step 104) is illustrated in FIG. 4.

According to the first check 201 ("is elapsed time since last recalibration<T_max?"), recalibration is trigged if the elapsed time after the latest re-/calibration has exceeded a certain threshold T_max. According to the second check 202 ("is the change in BP compared to last recalibration<$\Delta$BP_max?"), recalibration is triggered if the difference between the estimated BP and the BP of the latest reference measurement has exceeded a certain threshold $\Delta$BP_max. These first two checks are optional. They represent conditions for ensuring that recalibration is done at least once within a certain time interval (e.g. 2 hours) or if significant BP changes occur.

Figure 5:
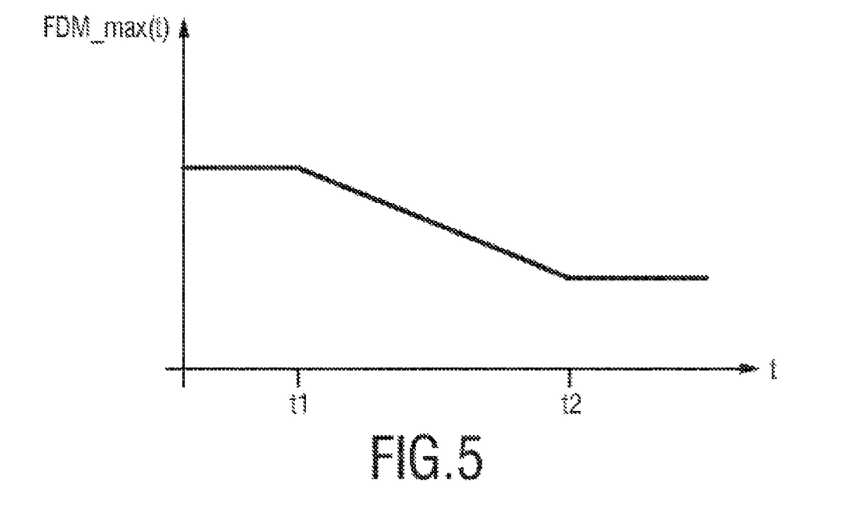
FIG. 5 shows a flow chart of a third embodiment of a method according to the present invention.

An essential element of the procedure is to check whether individual estimated BP values for the different feature are still in good agreement. If this is not the case it is a strong indication that not all features are accurately estimating BP. Therefore, a certain feature divergence metric (FDM) is defined (step 203) and compared to a certain threshold FDM_max (step 204). In case the FDM value exceeds the threshold, the recalibration condition ("Is FDM<FDM_max (t)?") is fulfilled (step 205) and a recalibration is triggered (see FIG. 3); otherwise (step 206), the recalibration is not fulfilled. As an alternative option, FDM_max can be time-varying. The more time has elapsed since the last re-/calibration, the lower the threshold is. An example of a time-varying threshold FDM_max(t) is illustrated in FIG. 5, where after a certain time t1 after recalibration, FDM_max is linearly decreased until time t2, after which it is kept constant again. Various other ways of threshold trajectories are possible.

In a preferred embodiment FDM is defined as the range of estimate BP values from all features, i.e. the difference between the maximum value from the estimated BP values of all features and the minimum value from the estimated BP values of all features. Alternative options to define FDM can be the standard deviation, the interquartile range, the mean absolute difference, the median absolute deviation, or the average absolute deviation of the estimated BP values of all features.

In a fifth step 105 of the method shown in FIG. 3, recalibration is performed. Recalibration is performed analogously as the initial calibration in step 102. Typically, the number of BP reference measurements conducted during recalibration is somewhat less compared to initial calibration.

Finally, the loop is closed and the cycle starts again in the third step 103.

Figure 6:
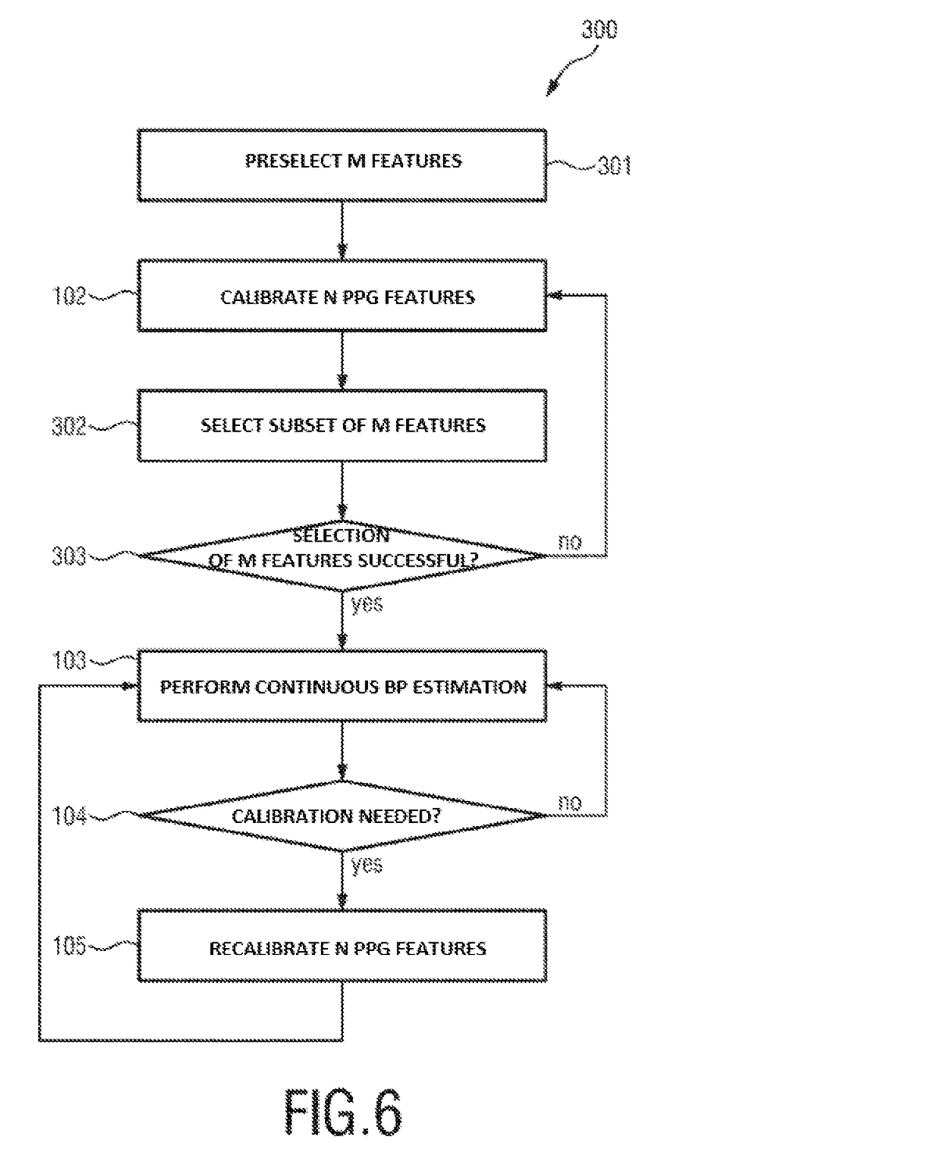
FIG. 6 shows a diagram of a time-varying divergence threshold.

Another embodiment of the method 300 according to the present invention, which deals with automatic recalibration of multiple features that are used for continuous BP estimation, is illustrated in the flowchart shown in FIG. 6. However, the essential difference compared to first embodiment shown in FIG. 3 is that after preselecting a large pool of M features (step 301, similar to step 101 of the first embodiment shown in FIG. 3) and after the initial recalibration step 102 a subset of the best N features is selected in step 302 and it is checked ("feature selection successful") in step 303 if the feature selection of the N features has been successful. The purpose of this element is to improve the robustness against inter-patient variability. By selecting a smaller subset of the best N features based on the initial calibration results, the set of features is tailored to the individual patient. This is not the case for the first embodiment, where a fixed set of features is utilized for all patients.

Figure 7:
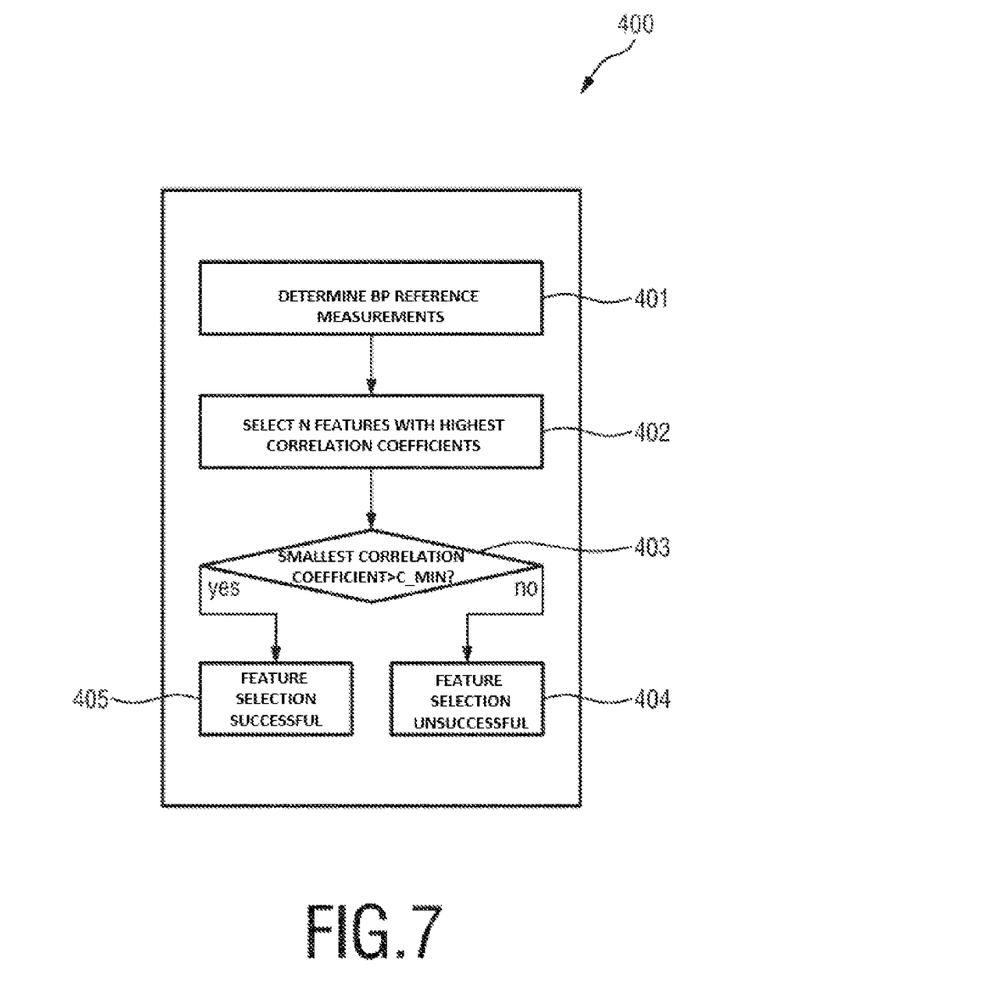
FIG. 7 shows a flow chart of a fourth embodiment of a method according to the present invention.

The procedure 400 for selecting the best N features out of the large pool of M features (i.e. an embodiment of steps 302 and 303 of the method 300 shown in FIG. 6) is illustrated in FIG. 7. The remaining steps in FIG. 6 are identical as in FIG. 3 and are described in the first embodiment.

As a criterion for ranking the M preselected features, the correlation with BP is chosen. Based on the feature values and BP reference values obtained during the calibration procedure, the correlation coefficient for each feature with respect to the BP reference measurements is determined in step 401. Afterwards, the N features with the highest correlation coefficients are selected in step 402. In step 403 it is checked ("Is smallest correlation coefficient>C_min?") if the correlation coefficient of the weakest feature does not exceed a certain minimum requirement (C_min), e.g. C_min=0.7, the output of the feature selection is denoted unsuccessful (step 404). Otherwise (step 405) the outcome is denoted successful. If the outcome of feature selection is unsuccessful, initial calibration can be repeated, such that more BP reference measurements are obtained.

By choosing a high correlation with BP as criterion for selecting a feature, a linear relation between the feature and BP is assumed. However, if the relation between a particular feature and BP is strong, but non-linear, then the correlation coefficient can be very low. Therefore, if for one or more features the mathematical model for relating the feature to BP is non-linear, then the regression error, which is obtained by fitting the feature values to the reference BP values obtained during calibration, is chosen as an alternative criterion for ranking the M preselected features.

As another alternative, the feature selection process can be improved by utilizing the signal-to-noise ratio of the measured features. For example, if the signal-to-noise ratio of the measured features is low, then the measured correlation coefficient or the measured regression error can be penalized by proper weighting factors. This prevents a noisy feature, which accidentally has a good correlation factor or a low regression error, from being selected. The signal-to-noise ratio of a feature can be measured e.g. by means of the standard deviation or sample variance.

Figure 8:
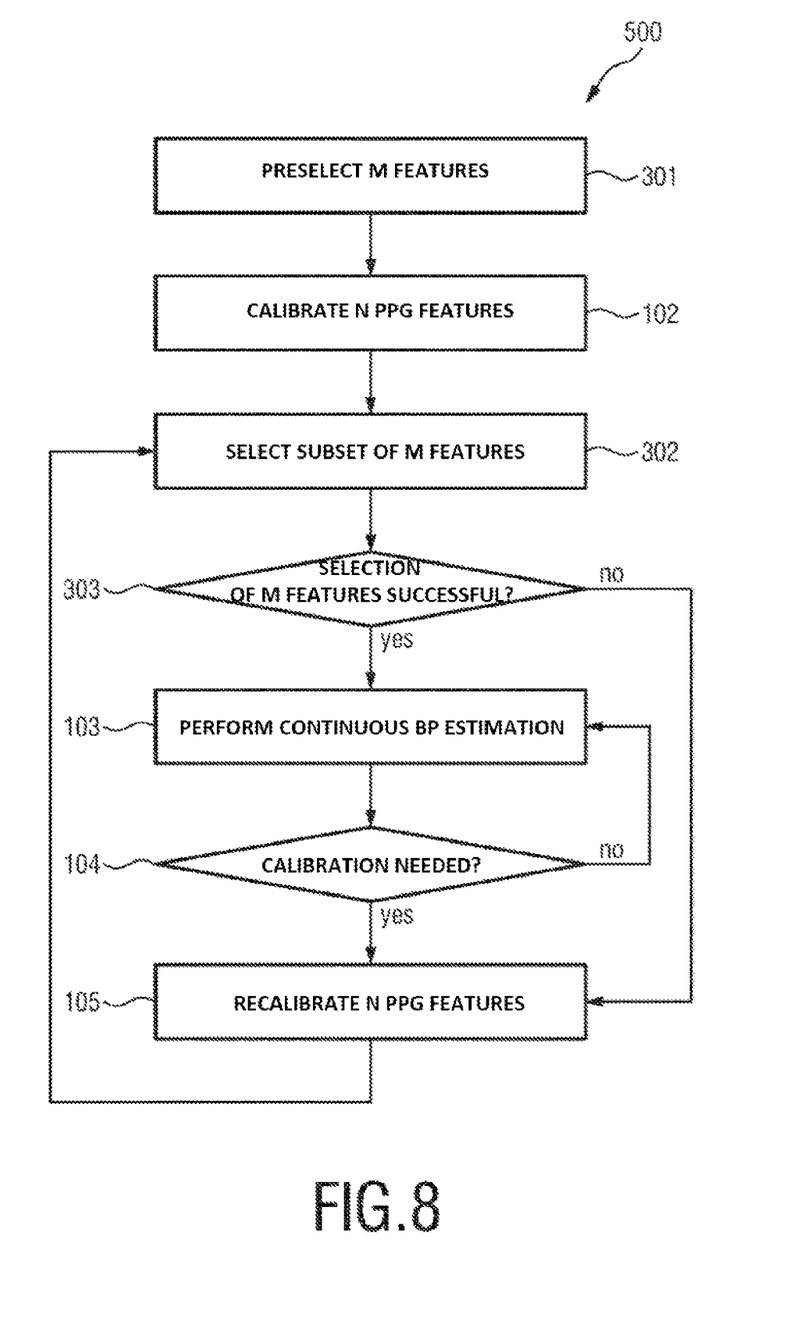
FIG. 8 shows a flow chart of a fifth embodiment of a method according to the present invention.

FIG. 8 shows a flow chart of another embodiment of a method 500 according to the present invention. Also this embodiment deals with automatic recalibration of multiple features that are used for continuous BP estimation. However, the essential difference compared to the embodiment shown in FIG. 6 is that the selection of a subset of the best N features out of a large pool of M features is conducted after each recalibration step. This is called dynamic feature selection. The purpose of this element is to improve, compared to the embodiment shown in FIG. 6, the robustness against intra-patient variability, i.e. physiological changes of the vascular system that occur in time. By selecting a smaller subset of the best N features based on each recalibration results, the set of features is tailored not only to the individual patient, but also to physiological changes of that patient over time. This is not the case for embodiment shown in FIG. 6, where a selection of the best N features for an individual patient is conducted only once after initial calibration. The individual steps shown in FIG. 8 are identical to those in FIG. 6 and are described in above illustrated embodiments.

The present invention may be used in all clinical settings, e.g. the general ward, in medium care, and in the operating room and intensive care unit for patients not requiring an arterial line.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable non-transitory medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. An apparatus for determining blood pressure of a subject, comprising:
 a sensor signal input configured to obtain an arterial pulse wave sensor signal of the subject;
 a feature extraction unit configured to extract multiple features from the obtained arterial pulse wave sensor signal;
 an estimation unit configured to determine multiple blood pressure estimation values for one or more extracted features and to determine the subject's blood pressure from said multiple blood pressure estimation values, wherein each of the multiple blood pressure estimation values is associated a corresponding one or more extracted features of the arterial pulse wave sensor signal, and wherein at least a portion of the one or more extracted features are preselected based on one or more data collection studies on the subject;
 a calibration unit configured to calibrate, using one or more computer processors, the estimation unit based on blood pressure reference measurements; and
 a calibration trigger unit configured to trigger the calibration by the calibration unit if the multiple blood pressure estimation values diverge more than a divergence limit.

2. The apparatus as claimed in claim 1,
 wherein said calibration trigger unit is configured to determine a feature divergence metric, the feature divergence metric representing a metric for a difference between the multiple blood pressure estimation values.

3. The apparatus as claimed in claim 1,
 wherein said calibration trigger unit is configured to trigger calibration if an average difference, a maximum difference or a standard deviation of the differences of a predetermined number or all of said multiple blood pressure estimation values exceeds a divergence threshold.

4. The apparatus as claimed in claim 3, wherein said calibration trigger unit is configured to use a predetermined or time-varying divergence threshold, wherein the time-varying divergence threshold is reduced with time since a last calibration.

5. The apparatus as claimed in claim 1,
 wherein said estimation unit is configured to determine the subject's blood pressure by taking an average or median of some or all of said multiple blood pressure estimation values.

6. The apparatus as claimed in claim 1, wherein said estimation unit is configured to determine the subject's blood pressure by taking a weighted average of some or all of said multiple blood pressure estimation values, wherein weights used for said weighted average are determined based on a correlation between the subject's blood pressure and a corresponding feature, wherein said correlation between the subject's blood pressure and a corresponding extracted feature is determined based on the obtained blood pressure reference measurements.

7. The apparatus as claimed in claim 1,
 wherein said calibration unit is configured to perform, using the one or more computer processors, an initial calibration of the estimation unit for the multiple features and to select a subset of extracted features from the multiple features based on a correlation between a subject's blood pressure and a corresponding feature and
 wherein said estimation unit is configured to determine the multiple blood pressure estimation values for individual extracted features and/or groups of extracted features of said subset.

8. The apparatus as claimed in claim 7,
 wherein said calibration unit is configured to repeat, using the one or more computer processors, a calibration of the estimation unit for some or all extracted features if one or more correlation values of said correlation for one or more features and the subject's blood pressure are below a correlation threshold.

9. The apparatus as claimed in claim 7,
wherein said calibration unit is configured to repeat, using the one or more computer processors, the calibration of the estimation unit for some or all extracted features if one or more correlation values of said correlation for one or more features and the subject's blood pressure are below a correlation threshold.

10. A method for determining blood pressure of a subject, comprising:
- obtaining an arterial pulse wave sensor signal of the subject;
- extracting multiple features from the obtained arterial pulse wave sensor signal;
- determining multiple blood pressure estimation values for individual extracted features and/or groups of extracted features;
- determining the subject's blood pressure from the multiple blood pressure estimation values, wherein each of the multiple blood pressure estimation values is associated a corresponding one or more extracted features of the obtained arterial pulse wave sensor signal, and wherein at least a portion of the one or more extracted features are preselected based on one or more data collection studies on the subject;
- calibrating the determining of the multiple blood pressure estimation values based on blood pressure reference measurements; and
- triggering calibration if the multiple blood pressure estimation values diverge more than a divergence limit.

\* \* \* \* \*